United States Patent [19]

Brown et al.

[11] Patent Number: 4,831,046

[45] Date of Patent: May 16, 1989

[54] TETRAZOLE DERIVATIVES OF 1,3-DIOXANE AND THROMBOXANE $A_2$ ANTIGONIZING USE THEREOF

[75] Inventors: George R. Brown, Wilmslow; Michael J. Smithers, Macclesfield, both of United Kingdom

[73] Assignee: Imperial Chemical Industries PLC, London, England

[21] Appl. No.: 861,334

[22] Filed: May 9, 1986

[30] Foreign Application Priority Data

May 10, 1985 [GB] United Kingdom ............... 8511895

[51] Int. Cl.$^4$ .................... A61K 31/41; C07D 405/06
[52] U.S. Cl. .................... 514/381; 548/252; 544/109; 544/366; 546/210; 514/255; 514/340; 514/236.2
[58] Field of Search ............ 548/252; 514/381, 255, 514/227, 340; 544/109, 366; 546/210

[56] References Cited

U.S. PATENT DOCUMENTS 3,600,437  8/1971  Marshall ..................... 548/252 X
3,883,513  5/1975  Hess et al. ..................... 548/252

FOREIGN PATENT DOCUMENTS 0094239  11/1983  European Pat. Off. .

OTHER PUBLICATIONS

Buchanan et al., J. of Med. Chem., 12, (1969), p. 1001.

*Primary Examiner*—David B. Springer
*Attorney, Agent, or Firm*—Cushman, Darby & Cushman

[57] ABSTRACT

The invention describes various novel tetrazole derivatives of the formula I in which $R^1$ and $R^2$ are independently hydrogen, trifluoromethyl or (1–6C)alkyl (but $R^1$ and $R^2$ is not greater than 6 carbon atoms), or $R^1$ is optionally substituted phenyl and $R^2$ is hydrogen, Y is vinylene, n is 1 or 2 and m is 1, 2 or 3, or a pharmaceutically acceptable salt thereof, for use in conjunction with their pharmaceutical compositions in the treatment of various pulmonary and/or vascular disorders. Also described are various processes and intermediates for the manufacture of the novel compounds.

11 Claims, No Drawings

TETRAZOLE DERIVATIVES OF 1,3-DIOXANE AND THROMBOXANE $A_2$ ANTIGONIZING USE THEREOF

This invention concerns novel tetrazole derivatives and, more particularly, novel 5-[(4-o-hydroxyphenyl-1,3-dioxan-5-yl)alkenyl]-1(H)-tetrazoles which antagonise one or more of the actions of thromboxane $A_2$ (hereafter referred to as "$TXA_2$") and which are of value as therapeutic agents.

It is known that $TXA_2$ is a potent aggregator of blood platelets and a powerful vasoconstrictor. $TXA_2$ is also a potent constrictor of bronchial and tracheal smooth muscle. $TXA_2$ may therefore be involved in a wide variety of disease conditions, for example ischaemic heart disease such as myocardial infarction, angina, cerebrovascular disease such as transient cerebral ischaemia, migraine and stroke, peripheral vascular disease such as atherosclerosis, microangiopathy, hypertension and blood cotting defects due to lipid imbalance, and pulmonary disease such as pulmonary embolism, bronchial asthma, bronchitis, pneumonia, dyspnoea and emphysema. Accordingly, compounds which antagonise the actions of $TXA_2$ may be expected to have therapeutic value in the prevention or treatment of any one or more of the above mentioned diseases or any other disease conditions in which it is desirable to antagonise the actions of $TXA_2$.

Certain 4-phenyl-1,3-dioxan-5-ylalkenoic acids are disclosed in European patent application, publication No. 94239, as possessing $TXA_2$ antagonist properties.

According to the invention there is provided a 5-[(4-o-hydroxyphenyl-1,3-dioxan-5yl)alkenyl]-1(H)-tetrazole of the formula I set out hereinafter wherein $R^1$ and $R^2$ are independently selected from hydrogen, (1–6C)alkyl and trifluoromethyl, provided that $R^1$ and $R^2$ take together contain no more than 6 carbon atoms, or $R^1$ is phenyl optionally bearing one or two substituents independently selected from halogeno, trifluoromethyl, cyano, nitro and (1–4C)alkoxy, and $R^2$ is hydrogen; Y is vinylene; n is 1 or 2; and m is 1,2 or 3; and the groups at positions 4 and 5 of the dioxane ring in formula I have cis-relative stereochemistry; or a pharmaceutically acceptable salt thereof.

It will be appreciated that the compounds of formula I contain at least two asymmetric carbon atoms (i.e. the carbon atoms at position 4 and 5 of the dioxane ring) and may exist and be isolated in racemic and optically active forms. In addition, the compounds of formula I can exist, and may be isolated, in separate stereoisomeric forms ('E' and 'Z') about the vinylene group Y. It is to be understood that the present invention encompasses any racemic, optically active or stereoisomeric form, or mixtures thereof, which is capable of antagonising one or more of the actions of $TXA_2$, it being well known in the art how to prepare individual optical isomers (for example by synthesis from optically active starting materials or resolution of a racemic form) and individual 'E' and 'Z' stereoisomers (for example by chromatographic separation of a mixture thereof), and how to determine the $TXA_2$ antagonist properties using the standard tests described hereafter.

Although a particular relative configuration is shown in the accompanying formulae, it is to be understood that it does not necessarily correspond to the absolute configuration.

A particular value for $R^1$ or $R^2$ when it is (1–6C)alkyl is, for example, methyl, ethyl, propyl, isopropyl, butyl or t-butyl. Particular combinations of values for $R^1$ and $R^2$ together are, for example $R^1$ is hydrogen, methyl, ethyl, isopropyl, t-butyl or trifluoromethyl and $R^2$ is hydrogen, methyl or trifluoromethyl; and $R^1$ is phenyl optionally substituted as defined above, and $R^2$ is hydrogen.

Particular values for optional substituents which may be present on $R^1$ when it is phenyl are, for example, for halogeno: fluoro, chloro or bromo, and for (1–4C)alkoxy: methoxy or ethoxy.

In general m is preferably 2 or 3 and n is preferably 1.

Preferred values for $R^1$ and $R^2$ together include, for example: $R^1$ and $R^2$ are both hydrogen or methyl; $R^1$ is trifluoromethyl, isopropyl or t-butyl and $R^2$ is hydrogen; and $R^1$ is phenyl bearing a chloro, cyano, trifluoromethyl, nitro or methoxy substituent, and $R^2$ is hydrogen.

Y is preferably cis-vinylene.

A preferred group of compounds according to the invention comprises those compounds of formula II wherein $R^3$ and $R^4$ are both methyl, or $R^3$ is isopropyl, t-butyl, trifluoromethyl or phenyl bearing a chloro or cyano substituent, and $R^4$ is hydrogen; and p is 2 or 3; or a pharmaceutically acceptable salt thereof.

Particular pharmaceutically acceptable salts of compounds of formula I are, for example, alkali metal and alkaline earth metal salts, such as lithium, sodium, potassium, magnesium and calcium salts, aluminium and ammonium salts, and salts with organic amines and quarternary bases forming physiologically acceptable cations, such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

Typical compounds of the invention are described in the accompanying Examples. Of these, the tetrazoles described in Examples 5 and 8, or a pharmaceutically acceptable salt thereof, are of especial interest.

The compounds of formula I may be manufactured by conventional procedures of organic chemistry well known in the art for the manufacture of structurally analogous compounds. Such procedures are provided as a further aspect of the invention and are illustrated by the following processes in which $R^1$, $R^2$, n, m and Y have any of the meanings defined hereinabove:

(A) An aldehyde of the formula III is reacted with a Wittig reagent of the formula IV wherein $R^1$ is (1–6C)-alkyl or aryl (especially phenyl) and $M^+$ is a cation, for example an alkali metal cation such as the lithium, sodium or potassium cation.

The process in general produces predominantly compounds of formula I in which the substituents adjoining the vinylene group have predominantly cis-relative stereochemistry i.e. the "Z" isomers. However, the compounds of formula I having trans-relative stereochemistry may also be obtained from the process by conventional separation of the mixture of cis- and trans-isomers first obtained.

The process is conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, −80° C. to 40° C., but may be conveniently performed at or near room temperature, that is in the range 0° to 35° C.

(b) A nitrile of the formula V is reacted with an azide.

A particularly suitable azide is, for example, an alkali metal azide such as sodium or potassium azide, preferably together with an ammonium halide, for example ammonium chloride, ammonium bromide or triethylammonium chloride. The process is preferably carried out in a suitable polar solvent, for example N,N-dimethylformamide or N-methylpyrrolidone and, conveniently, at a temperature in the range, for example, 50° to 160° C.

(c) A phenol derivative of the formula VI, wherein R″ is a suitable protecting group, for example, (1-6C)alkyl (such as methyl or ethyl), acyl (such as acetyl, benzoyl, methanesulphonyl or p-toluenesulphonyl), allyl, tetrahydropyran-2-yl or trimethylsilyl, is deprotected.

The precise deprotection conditions used depend on the nature of the protecting group R″. Thus, for example, when it is methyl or ethyl the deprotection may be carried out by heating with sodium thioethoxide in a suitable solvent (such as N,N-dimethylformamide or 1,3-dimethyl-3,4,5,6-tetrahydro-2(1H)-pyrimidinone) at a temperature in the range, for example, 50°-160° C. Alternatively, an ethyl or methyl protecting group may be removed by reaction with lithium diphenylphosphide in a suitable solvent (such as tetrahydrofuran or t-butyl methyl ether) at a temperature in the range, for example, 0°-60° C. When the protecting group is acyl it may be removed, for example, by hydrolysis in the presence of a base (such as sodium or potassium hydroxide) in a suitable aqueous solvent [such as an aqueous (1-4C)alkanol] at a temperature in the range, for example, 0°-60° C. When the protecting group is allyl or tetrahydropyran-2-yl, it may be removed, for example, by treatment with strong acid such as trifluoroacetic acid and when it is trimethylsilyl, it may be removed, for example, by reaction with aqueous tetrabutylammonium fluoride or sodium fluoride, using a conventional procedure.

(d) For a compound of formula I wherein $R^1$ or $R^2$ are other than trifluoromethyl, reacting an erythrodiol derivative of the formula VII, wherein one of $Q^1$ and $Q^2$ is hydrogen and the other is hydrogen or a group of the formula —$CR^aR^b$.OH (wherein $R^a$ and $R^b$ are the same or different (1-6C)alkyl), with a carbonyl compound of the formula $R^5$.CO.$R^6$ (wherein $R^5$ and $R^6$ have the same meanings as $R^1$ and $R^2$ respectively apart from trifluoromethyl), or with an acetal, hemiacetal or hydrate thereof.

The carbonyl compound of the formula $R^5$.CO.$R^6$ [or its hydrate, or its acetal or hemiacetal with a (1-4C)alkanol (such as methanol or ethanol)] is generally used in excess.

The reaction is generally performed in the presence of an acid catalyst, such as hydrogen chloride, hydrogen bromide, sulphuric acid, phosphoric acid, methanesulphonic acid, p-toluenesulphonic acid or an acidic resin, conveniently in the presence of a suitable solvent or diluent, such as toluene, xylene or an ether, for example tetrahydrofuran, dibutyl ether, methyl t-butyl ether or 1,2-dimethoxyethane, and at temperature in the range, for example 0° to 80° C.

Those starting materials of formula VII wherein $Q^1$ and $Q^2$ are both hydrogen may be obtained, for example, by mild acid catalysed hydrolysis or alcoholysis of the dioxane ring of a compound of formula I wherein $R^1$ and $R^2$ are both alkyl, such as methyl or ethyl, obtained by another process herein. The hydrolysis or alcoholysis will normally be carried out a temperature in the range 10° to 80° C. using an aqueous mineral acid such as hydrochloric acid, in an alkanol (such as ethanol or 2-propanol) or an ether (such as tetrahydrofuran), as solvent.

The starting materials of formula VII wherein one of $Q^1$ and $Q^2$ is hydrogen and the other is a group of the formula —$CR^aR^b$.OH are intermediates in the above-mentioned formation of the starting materials of formula VII wherein $Q^1$ and $Q^2$ are both hydrogen. However, said intermediates are not normally isolated or characterised. Accordingly, the invention also provides a modification of process (d) which comprises reacting a compound of formula I wherein one of $R^1$ and $R^2$ is hydrogen, methyl or ethyl (preferably methyl or ethyl) and the other is methyl or ethyl with an excess of a compound of the formula $R^5$.CO.$R^6$ (wherein $R^5$ and $R^6$ have the meanings defined above) or of an acetal, hemiacetal or hydrate thereof in the presence of an acid-catalyst (such as one of those given above), conveniently at a temperature in the range, for example, 10° to 80° C. and optionally in the presence of a suitable solvent or diluent (such as one of those given above).

The starting materials for use in the above processes may be made by general procedures of organic chemistry, known for the preparation of structurally related compounds, for example as described in European patent application, publication No. 94239. Thus, the aldehydes of formula III may be obtained by one of the methods described in the following Examples.

The nitriles of formula V may be obtained, for example, by substituting the appropriate ylid of the formula $R_3P=CH.(CH_2)_m.CN$ for the ylid of formula IV in the Wittig reaction described in process (a) above. Alternatively, the nitriles of formula V may be obtained by conventional dehydration of the corresponding amides of formula VIII, which are themselves obtainable by ammonolysis of the methyl esters of their corresponding carboxylic acids, which are either known per se or may be made by analogy with known, structurally analogous, carboxylic acid esters.

The necessary Wittig reagents of formula IV may be obtained by conventional procedures, for example by treating the corresponding phosphonium halides with a strong base. Such as sodium hydride, lithium diisopropylamide, potassium t-butoxide or butyllithium. They are generally formed in situ just prior to carrying out the condensation process (a) above.

When a salt of a compound of formula I is required, it may be obtained by reaction with the appropriate base affording a physiologically acceptable cation, or by any other conventional procedure.

Further, when an optically active form of a compound of formula I is required, one of the aforesaid processes may be carried out using an optically active starting material. Alternatively, the racemic form of a compound of formula I may be reacted with an optically active form of a suitable organic base, for example ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said compound of formula I may be liberated by treatment with acid using a conventional procedure for example using an aqueous mineral acid such as dilute hydrochloric acid.

Many of the intermediates defined herein are novel and are provided as further separate features of the invention.

As stated earlier, the compounds of formula I are antagonists of one or more of the actions of $TXA_2$, for example certain of its actions on blood platelets, the vasculature and/or the lung. The antagonism may be demonstrated in one or other of the following standard tests:

(a) The rabbit aortal strip model devised by Piper and Vane (Nature, 1969, 223, 29–35) using as agonist a freshly prepared sample of $TXA_2$, generated by addition of arachidonic acid (25 μg) to citrated, platelet rich rabbit plasma (250 μl) and allowing the mixture to aggregate fully over 90 seconds before use; alternatively the $TXA_2$ mimetic agent known as U46619 (described by R L Jones et alia, in "Chemistry, Biochemistry and Pharmacological Activity of Prostanoids" edited by S M Roberts and F Scheinmann, at page 211, Pergamon Press, 1979) may be used as the agonist;

(b) a blood platelet aggregation test based on that described by Born (Nature, 1962, 194, 927–929) and involving:

(i) aggregating human, citrated platelet-rich plasma by addition of the $TXA_2$ mimetic agent U46619 so that a dose-response curve is generated;

(ii) generating a dose-response curve for U46619 stimulated platelet aggregation in the presence of increasing amounts of test compound (generally in the range, $10^{-5}$M to $10^{-10}$M); and (iii) calculating a $K_B$ value indicating potency of $TXA_2$ antagonism for the test compound averaged over several concentrations, from the calculated 50% response value for U46619 aggregation in the presence and absence of test compound; and (c) a bronchoconstriction test involving measuring the inhibition by a test compound of the bronchoconstriction induced in the Konzett-Rossler, anaesthetised guinea-pig model (as modified by Collier and James, Brit. J. Pharmacol., 1967, 30, 283–307) by intravenous administration of the $TXA_2$ mimetic agent, U46619 and involving:

(i) obtaining a cumulative dose-response curve to U46619 induced bronchoconstriction by intravenous administration of constant volumes of increasing concentrations of U46619 (0.2–4 μg/kg) in physiological saline solution and expressing bronchoconstriction as the maximum of that theoretically obtainable with no air flow to the test animal;

(ii) generating a cumulative dose-response curve to U46619 induced bronchoconstriction at 30 minute intervals for 3 hours after oral dosing of test compound; and (iii) calculating a dose-ratio for the test compound (that is the ratio of concentration of U46619 required to cause 50% bronchoconstriction in the presence and absence of test compound) indicating the potency of $TXA_2$ antagonism.

The antagonism of the effects of $TXA_2$ on the vasculature may be demonstrated, for example, in rats in the following manner:

Male rats (Alderley Park strain) are anaesthetised with sodium pentobarbital and blood pressure is monitored at the carotid artery. The $TXA_2$ mimetic agent U46619 is administered intravenously via the jugular vein at 5 μg/kg to induce a 20–30 mm Hg (2640–3970 pascal) rise in systolic blood pressure. The process is repeated twice to establish reproducibility of response to U46619. A test compound is then administered either intravenously (via the jugular vein) or orally (via a cannula directly into the stomach) and the animal challenged with U46619, five minutes after dosing with test compound and then successively every ten minutes until the hypertensive effect of U46619 is no longer blocked. Further, the antagonism of the effects of $TXA_2$ in vivo may be demonstrated, for example, by assessing the effects of a test compound on the aggregation of blood platelets obtained after administration of test compound to a test animal such as a rabiit, rat, guinea pig or dog, using standard procedures similar to that described in (a) above. However, when the aggregation of dog platelets is being studied it is necessary to use a predetermined, threshold concentration of the platelet aggregrant adenosine diphosphate (about $0.4-1.2 \times 10^{-6}M$) together with the $TXA_2$ mimetic agent, U46619.

By way of example, the compound 5-[3(Z)-5-([2,4,5-cis]-4-o-hydroxyphenyl-2-isopropyl-1,3-dioxan-5-yl)pentyl]-1(H)-tetrazole (described in Example 5 hereafter) possesses the following properties in certain of the above tests:

(a) $pA_2$ 7.32

(b) $K_B$ $4.56 \times 10^{-8}$M (c) dose ratio 25 at 50 μg/kg p.o.

In general, compounds of formula I show significant $TXA_2$ antagonist properties in one or more of the above mentioned tests i.e. test (a) $pA_2 > 6.0$; test (b) $K_B < 5 \times 10^{-6}$; test (c) dose ratio $> 5$ at 100 μg/kg p.o. In addition, compounds of formula I may show significant activity in the rat blood pressure test and/or in one or more of the ex vivo blood platelet tests referred to above. No significant adverse effects have been observed at the active doses in vivo.

As stated previously, the compounds of formula I may be used in the therapy or prevention of diseases or adverse conditions in warm-blooded animals in which it is desirable to antagonise one or more of the actions of $TXA_2$. In general, a compound of formula I will be administered for this purpose by an oral, rectal, intravenous, subcutaneous, intramuscular or inhalation route, so that a dose in the range, for example 0.01–5 mg/kg body weight, will be given up to four times per day, varying with the route of administration, the severity of the condition and the size and age of the patient under treatment.

The compounds of formula I will generally be used in the form of a pharmaceutical composition comprising a compound of formula I, or a pharmaceutically acceptable salt thereof, as defined hereinbefore, together with a pharmaceutically acceptable diluent or carrier. Such a composition is provided as a further feature of the invention and may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; and in the form of a powder together with one or more pharmaceutically acceptable inert solid diluents (such as lactose), for administration by insufflation.

The pharmaceutical compositions may be obtained by conventional procedures using pharmaceutically acceptable diluents and carriers well known in the art.

Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents known to be of value in diseases or conditions intended to be treated; for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an antihistamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

In addition to their use in therapeutic medicine, the compounds of formula I are also useful as pharmacological tools in the development and standardisation of test systems for the evaluation of the effects of $TXA_2$ in laboratory animals such as cats, dogs, rabbits, monkeys, rats and mice, as part of the search for new therapeutic agents. The compounds of formula I may also be used because of their $TXA_2$ antagonist properties in helping to maintain the viability of blood and blood vessels in warm-blooded animals (or parts thereof) under-going artificial extracorporeal circulation, for example during limb or organ transplant. When used for this purpose, a compound of formula I, or a physiologically acceptable salt thereof, will generally be administered so that a steady state concentration in the range, for example, 0.1 to 10 mg per liter is achieved in the blood.

The invention will now be illustrated by the following non-limiting Examples in which, unless otherwise stated:

(i) evaporation were carried out by rotary evaporation in vacuo;

(ii) operations were carried out at room temperature, that is in the range 18°–26° C.;

(iii) the progress of reactions was monitored by thin layer chromatography (TLC) on Merck 0.25 mm Kieselgel 60F 254 plates (Art. 5715); flash and medium pressure liquid chromatography was performed on Merck Kieselgel (Art 9385), monitoring by TLC or by UV absorption; these materials were obtained from E. Merck, Darmstadt, W. Germany;

(iv) yields are given for illustration only and are not necessarily the maximum attainable;

(v) NMR spectra were normally determined at 200 MHz in $CDCl_3$ using tetramethylsilane (TMS) as an internal standard, and expressed as chemical shifts (delta values) in parts per million relative to TMS using the following abbreviations for designation of major peaks: s, singlet; m, multiplet; t, triplet; br, board; d, doublet; when a single chemical shift value is given for a multiplet (m) this corresponds to the centre point of the signals making up the multiplet; and (vi) end-products were isolated as racemates, and characterized by NMR, microanalysis, mass spectroscopy and/or other standard procedures.

EXAMPLE 1

A solution of ([2,4,5-cis]-4-o-hydroxyphenyl-2-trifluoromethyl-1,3-dioxan-5-yl)acetaldehyde (419 mg) in dry tetrahydrofuran (THF) (5 ml) was added under argon with stirring and ice-cooling to a solution of the ylid prepared from (4-[1(H)-tetrazol-5-yl]butyl)triphenylphosphonium bromide (2.36 g) and potassium t-butoxide (1.13 g) in dry THF (25 ml). The mixture was stirred for 1 hour at 4° C., then 1 hour at ambient temperature and was then poured into ice-water (40 ml). The mixture obtained was extracted with 50% v/v ether/hexane (2×25 ml). The aqueous phase was acidified to pH 3 with 2M hydrochloric acid and extracted with ether (3×30 ml). The combined extracts were washed with water (3×25 ml), then with saturated brine (2×25 ml), dried ($MgSO_4$) and evaporated. The yellow oil obtained was purified by flash chromatography, eluting with toluene/ethyl acetate/acetic acid (50:50:2 v/v) to give 5-[4(Z)-6-([2,4,5-cis]-4-o-hydroxyphenyl-2-trifluoromethyl-1,3-dioxan-5-yl)hexenyl]-1(H)tetrazole as a solid foam (469 mg); NMR: 1.90 (3H, m), 2.00 (3H, m), 2.41 (1H, m), 2.92 (2H, t J=8 Hz), 4.01 (1H, br d J=11 Hz) 4.21 (1H, d J=11 Hz), 5.11 (1H, q J=3 Hz), 5.37 (3H, m), 6.85 (1H, d J=8 Hz), 6.90 (1H, t J=8 Hz), 7.13 (1H, t d J=8, 1 Hz), 7.24 (1H, d J=8 Hz); m/e 399 $(M+H)^+$.

The starting aldehyde was obtained as follows:

Ozone was passed through a solution of 5(Z)-7-([2,4,5-cis]-4-o-hydroxyphenyl-2-trifluoromethyl-1,3-dioxan-5-yl)heptenoic acid (A) (1.22 g) in ethyl acetate (50 ml) at −78° C. until a permanent blue colour developed. The solution was then flushed with argon until colourless. A solution of triphenylphosphine (1.26 g) in ethyl acetate (20 ml) was then added and the mixture was stirred for 1 hour at −78° C. and then at ambient temperature overnight. The mixture was evaporated. The residue was purified by flash chromatography, eluting with 25% v/v ethyl acetate in hexane, to give ([2,4,5-cis]-4-o-hydroxyphenyl-2-trifluoromethyl-1,3-dioxan-5-yl)acetaldehyde (448 mg), m.p. 138°–140° C.; NMR: 2.50 (1H, dd J=18, 3 Hz), 2.64 (1H, m), 2.98 (1H, dd J=18, 9 Hz), 4.20 (2H, m), 5.11 (1H, q J=3 Hz), 5.30 (1H, d J=2 Hz), 6.18 (1H, s), 6.80 (1H, dd J=8, 1 Hz), 6.93 (1H, td J=8, 1 Hz), 7.18 (2H, m), 9.60 (1H, s); m/e 290 $(M+)$.

The starting heptenoic acid A was itself obtained as follows:

(i) A solution containing (4,5-cis)-5-allyl-4-o-methoxyphenyl-2,2-dimethyl-1,3-dioxane (51.6 g), water (120 ml) and 2M hydrochloric acid (5.0 ml) in (THF) (400 ml) was heated with stirring at 70° C. for 2 hours. The mixture was poured into water (1 liter), then extracted with ether (3×500 ml). The combined extracts were washed with water (2×250 ml), then with brine (2×250 ml), dried ($MgSO_4$) and evaporated to give erythro-2-allyl-1-o-methoxyphenyl-1,3-propanediol (B) as a crystalline solid (43.69 g), m.p 59°–60° C.

(ii) A solution of p-toluenesulphonyl chloride (43.4 g) in dichloromethane (120 ml) was added during 30 minutes to a stirred solution of B (44.69 g) in dichloromethane (400 ml) containing triethylamine (31.50 ml) and maintained at 4° C. The mixture was stirred for a further 1 hour at 4° C. and then for 64 hours at ambient temperature before being diluted with ether (1.2 l). The subsequent mixture was washed successively with water (2×200 ml), 0.2M aqueous hydrochloric acid (200 ml), saturated brine (200 ml), 2% w/v aqueous sodium hydrogen carbonate (200 ml), water (2×200 ml) and then with saturated brine (200 ml). The organic phase was dried ($MgSO_4$) and evaporated. The oil obtained was triturated with 5% v/v ethyl acetate/hexane to give a solid which was recrystallised from 1:3 v/v ethyl acetate/hexane (500 ml). There was thus obtained 3-(erythro-2-allyl-1-o-methoxyphenyl-1,3-propanediol) p-toluenesulphonate ester (C) (54.4 g), m.p. 103°-104° C.

(iii) A solution of C (54.4 g) in dry THF (600 ml) was treated with anhydrous trifluoroacetaldehyde (prepared from 50 g of trifluoroacetaldehyde methyl hemiacetal) at −78° C. under argon. The mixture was stirred for 1 hour at −78° C. allowed to warm to ambient temperature and stirred for a further 1 hour. Anhydrous potassium carbonate (38.72 g) was added and the stirred mixture was heated at 70° C. for 16 hours. The mixture was separated by filtration and the residue was washed with further THF. Evaporation of the filtrate and flash chromatography of the residue, eluting with 2% v/v ethyl acetate/hexane, gave [2,4,5-cis]-5-allyl-4-o-methoxyphenyl-2-trifluoromethyl-1,3-dioxane (D) (35.0 g) as a crystalline solid, m.p. 43°-45° C.

(iv) Ozone was passed through a solution of D (35.0 g) in ethyl acetate (800 ml) at −78° C. until a permanent blue colour developed. The solution was then flushed with argon until colourless. A solution of triphenylphosphine (45.55 g) in ethyl acetate (200 ml) was added and the mixture was allowed to warm to ambient temperature overnight. After evaporation, ether (500 ml) was added to the residue and the insoluble triphenylphosphine oxide was removed by filtration. The filtrate was evaporated. The oil obtained was purified by flash chromatography, eluting with first 10% and then 25% v/v ethyl acetate/hexane, to give ([2,4,5-cis]-4-o-methoxyphenyl-2-trifluoromethyl-1,3-dioxan-5-yl)acetaldehyde (E) (33.25 g), m.p. 67°-68° C.

(v) A solution of E (33.25 g) in dry THF (150 ml) was added under argon with stirring and ice-cooling to a solution of the ylid prepared from (4-carboxybutyl)triphenylphosphonium bromide (121.05 g) and potassium t-butoxide (61.21 g) in dry THF (750 ml). The mixture was stirred for 1 hour at 4° C., then overnight at ambient temperature and was then poured into ice-water (1.5 l). The mixture obtained was extracted with 50% v/v ether/hexane (2×500 ml) to remove the bulk of neutral material. The aqueous phase was then acidified of pH 2-3 with 2M hydrochloric acid and extracted with ether (4×400 ml). These combined extracts were washed with water (3×250 ml), then with saturated brine (2×200 ml), dried (MgSO$_4$) and evaporated to give a give a yellow oil. Purification by flash chromatography, eluting with toluene/ethyl acetate/acetic acid (85:15:2 v/v) gave a solid (40.15 g). Recrystallisation from hexane (600 ml) gave 5(Z)-7-([2,4,5-cis]-4-o-methoxyphenyl-2-trifluoromethyl-1,3-dioxan-5-yl)heptenoic acid (F) (36.2 g), m.p. 104°-105.5° C.

(vi) F (19.4 g) was added to a stirred solution of sodium thioethoxide (25.2 g) in dry 1,3-dimethyl-3,4,5,6-tetrahydro-2(1H)-pyrimidinone (DMPU) (300 ml) at 80°-85° C. under argon. The mixture was stirred for 2.25 hours, cooled to 10° C. and poured into an ice-water mixture (1 liter). The aqueous mixture was extracted with dichloromethane (2×500 ml), acidified to pH3 with 2M hydrochloric acid and extracted with ether (3×500 ml). The combined extracts were washed with water (3×300 Ml), then with saturated brine (2×300 ml), then dried (MgSO$_4$) and the solvent evaporated. The oil obtained was purified by flash chromatography eluting with toluene/ethyl acetate/acetic acid (80:20:2 v/v). Recrystallisation from 15% v/v ether/hexane (150 ml) gave 5(Z)-7-([2,4,5-cis]-4-o-hydroxyphenyl-2-trifluoromethyl-1,3-dioxan-5-yl)heptenoic acid (A) (11.6 g), m.p. 93°-95° C.

The starting aldehyde may also be obtained as follows:

(i) A solution of [2,4,5-cis]-5-allyl-4-o-methoxyphenyl-2-trifluoromethyl-1,3-dioxane (D) (1.22 g) in dry THF (4 ml) was treated at 4° C. under argon with a solution of lithium diphenylphosphide [prepared from chlorodiphenylphosphine (2.23 g) and lithium metal (283 mg) in dry THF (12 ml.)]. The mixture was stirred for 15 minutes at 4° C., for 3 hours at 50° C., then cooled to 10° C. and poured into an ice-water mixture (50 ml). The aqueous mixture was acidified to pH 3 with 2M hydrochloric acid and extracted with ether (3×30 ml). The combined extracts were washed successively with water (4×15 ml) and saturated brine (15 ml), then dried (MgSO$_4$) and evaporated. The residual oil was purified by MPLC, eluting with hexane/ethyl acetate/acetic acid (82.5:17.5:0.1 v/v), to give [2,4,5-cis]-5-allyl-4-o-hydroxyphenyl-2-trifluoromethyl-1,3-dioxane (G), as a colourless oil which slowly crystallised to give solid (1.11 g), m.p 80°-81.5° C.; NMR 1.88 (1H, m), 2.00 (1H, m), 2.49 (1H, m), 4.02 (1H, dt J=12, 1.5 Hz), 4.33 (1H, dd J=12, 1 Hz), 5.05 (2H, m), 5.10 (1H, q J=3 Hz), 5.33 (1H, d J=2 Hz), 5.58 (1H, m), 6.41 (1H, s) 6.82 (1H, dd J=7, 1 Hz), 6.92 (1H, td J=7, 1 Hz), 7.11 (1H, dd J=7, 1.5 Hz), 7.20 (1H, td J=7, 1.5 Hz); m/e 306 (M+NH$_4$)+.

(ii) Ozone was passed through a solution of G (1.0 g) in ethyl acetate (75 ml) at −78° C. until a permanent blue colour developed. The solution was then flushed with argon until colourless. A solution of triphenylphosphine (1.37 g) in ethyl acetate (20 ml) was added and the mixture was stirred for 1 hour at −78° C. and then overnight at ambient temperature. The solvent was evaporated and the residue was purified by flash chromatography, eluting with 30% v/v ethyl acetate/hexane, to give ([2,4,5-cis]-4-o-hydroxyphenyl-2-trifluoromethyl-1,3-dioxan-5-yl)acetaldehyde as a crystalline solid (766 mg), m.p. 140°-142° C.; NMR 2.51 (1H, br dd J=18, 3 Hz), 2.64 (1H, m), 2.98 (1H, dd J=18, 9 Hz), 4.19 (2H, m), 5.11 (1H, q J=3 Hz), 5.32 (1H, d J=2 Hz), 6.17 (1H, s), 6.79 (1H, br d J=8 Hz), 6.93 (1H, td J=7, 1 Hz), 7.19 (2H, m), 9.61 (1H, s).

EXAMPLE 2

A solution of (4-o-hydroxyphenyl-2,2-dimethyl-1,3-dioxan-cis-5-yl)acetaldehyde (1.25 g) in dry THF (10 ml) was added under argon with stirring and ice-cooling to a solution of the ylid prepared from (4-[1(H)-tetrazol-5-yl]butyl)triphenylphosphonium bromide (7.01 g) and potassium t-butoxide (3.36 g) in dry THF (70 ml). The mixture was stirred for 1 hour at 4° C., then 1 hour at ambient temperature and was then poured into ice-water (100 ml). The mixture obtained was extracted with 50% v/v ether/hexane (2×50 ml). The aqueous phase was acidified with acetic acid and extracted with ether (3×50 ml). The combined extracts were washed with water (3×25 ml), then with saturated brine (2×25 ml), dried (MgSO$_4$) and evaporated. The yellow oil obtained was purified by flash chromatography, eluting with toluene/ethyl acetate/acetic acid (75:25:2 v/v) to give 5-[4(Z)-6-(4-o-hydroxyphenyl-2,2-dimethyl-1,3-dioxan-cis-5-yl)hexenyl-1(H)-tetrazole as a white, solid foam (1.147 g); NMR: 1.67 (6H, s), 1.88 (6H, m), 2.68 (1H, m), 2.94 (2H, m), 3.90 (1H, brd J=12 Hz), 4.25 (1H, dm J=11 Hz), 5.32 (2H, m), 5.52 (1H, d J=2 Hz), 6.88 (2H, m), 7.00 (1H, br d J=7 Hz), 7.17 (1H, td J=8, 1 Hz); m/e 359 (M+H)+.

The starting acetaldehyde was obtained as follows:

(i) (4,5-Cis)-5-allyl-4-o-methoxyphenyl-2,2-dimethyl-1,3-dioxane (9.70 g) was added to a stirred solution of sodium thioethoxide (18.6 g) in dry DMPU (150 ml) at 125°-130° C. under argon. The mixture was stirred for 1.25 hours, cooled to 10° C. and poured into a mixture of ice and water (1 liter). The aqueous mixture was acidified with acetic acid and extracted with ethyl acetate (3×400 ml). The combined extracts were washed with water (3×250 ml), then with saturated brine (1×250 ml), dried (MgSO$_4$) and evaporated. The oil obtained was purified by flash chromatography eluting with 12.5% v/v ethyl acetate/hexane to give (4,5-cis)-5-allyl-4-o-hydroxyphenyl-2,2-dimethyl-1,3-dioxane (9.01 g), m.p. 50°-52° C.; NMR: 1.55 (3H, s), 1.58 (3H, s), 1.64 (1H, m), 2.00 (1H, m), 2.57 (1H, m), 3.91 (1H, dd J=12, 2 Hz), 4.14 (1H, dm J=12 Hz), 5.02 (2H, m), 5.45 (1H, d J=3 Hz), 5.60 (1H, m), 6.87 (3H, m), 7.17 (1H, m), 8.47 (1H, s); m/e 248 (M$^+$).

(ii) Ozone was passed through a solution of (4,5-cis)-5-allyl-4-o-hydroxyphenyl-2,2-dimethyl-1,3-dioxane (7.20 g) in ethyl acetate (200 ml) at −78° C. until a permanent blue colour developed. The solution was then flushed with argon until colourless. A solution of triphenylphosphine (11.0 g) in ethyl acetate (75 ml) was then added and the mixture was stirred for 1 hour at −78° C. and then overnight at ambient temperature. The mixture was evaporated and the residue purifed by flash chromatography eluting with 27.5% v/v ethyl acetate in hexane, to give (4-o-hydroxyphenyl-2,2-dimethyl-1,3-dioxan-cis-5-yl)acetaldehyde, as a colourless oil (7.00 g); NMR: 1.55 (3H, s), 1.59 (3H, s), 2.44 (1H, m), 3.08 (1H, m), 3.80 (1H, dd J=12, 2 Hz), 4.28 (1H, dm J=12 Hz), 5.44 (1H, d J=3 Hz), 6.87 (3H, m), 7.17 (1H, m), 8.30 (1H, s), 9.65 (1H, s); m/e 250 (M$^+$);

EXAMPLE 3

A solution of 5-[4(Z)-6-(4-o-hydroxyphenyl-2,2-dimethyl-1,3-dioxan-cis-5-yl)hexenyl]-1(H)-tetrazole (620 mg) in isobutyraldehyde (1.57 ml) was treated with p-toluenesulphonic acid (5 mg) and stirred for 2 hours. Ether (50 ml) was then added and the mixture was extracted with 0.1M potassium hydroxide (1×40 ml). The aqueous extract was acidified with acetic acid and the extracted with ether (3×25 ml). The combined extracts were washed with water (3×15 ml). then with saturated brine (2×15 ml), then dried (MgSO$_4$) and evaporated. The residue was purified by medium pressure liquid chromatography, eluting with hexane/ethyl acetate/acetic acid (57.5: 42.5:1 v/v) to give 5-[4(Z)-6-([2,4,5-cis]-4-o-hydroxyphenyl-2-isopropyl-1,3-dioxan-5-yl)hexenyl]-1(H)-tetrazole, as a white, solid foam (413 mg); NMR: 1.04 (6H, d J=7 Hz), 1.72 (1H, m), 1.88 (3H, m), 2.07 (3H, m), 2.60 (1H, m), 2.94 (2H, m), 3.98 (1H, dm J=11 Hz), 4.15 (1H, dd J=12, 1 Hz), 4.60 (1H, d J=4 Hz), 5.26 (1H, d J=2 Hz), 5.33 (2H, m), 6.89 (2H, m), 7.00 (1H, dd J=7, 1.5 Hz), 7.18 (1H, m), m/e 372 (M$^+$).

EXAMPLE 4

A solution of (4-o-hydroxyphenyl-2,2-dimethyl-1,3-dioxan-cis-5-yl)acetaldehyde (2.50 g) in dry THF (15 ml) was added under argon with stirring and ice-cooling to a solution of the yield prepared from (3-[1(H)-tetrzol-5-yl]propyl)triphenylphosphonium bromide (11.33 g) and potassium t-butoxide (5.60 g) in dry THF (100 ml). The mixture was stirred for 1 hour at 4° C., then 1 hour at ambient temperature and was then poured into ice-water (200 ml). The aqueous mixture obtained was extracted with 50% v/v ether/hexane (2×100 ml) and the extracts discarded. The aqueous phase was then acidified with glacial acetic acid and extracted with ether (3×100 ml). These combined extracts were washed with water (4×100 ml), then with saturated brine (3×50 ml), dried (MgSO$_4$) and evaporated. The yellow oil obtained was purified by flash chromatography, eluting with ether/hexane/acetic acid (85:15:1 v/v), to give 5-[3(Z)-5-(4-o-hydroxyphenyl-2,2-dimethyl-1,3-dioxan-cis-5-yl)pentenyl]-1(H)-tetrazole, as a white, solid foam (2.54 g); NMR: 1.63 (3H, s), 1.66 (3H, s), 1.78 (2H, m), 2.61 (3H, m) 3.11 (2H, t J=7 Hz), 3.81 (1H, dd J=12, 1 Hz), 4.22 (1H, dm J=12 Hz), 5.34 (2H, m), 5.52 (1H, d J=2 Hz), 6.87 (2H, m), 7.02 (1H, dd J=1.5 Hz), 7.16 (1H, td J=8, 1.5 Hz); m/e 345 (M+H)$^+$.

The starting phosphonium salt was obtained as follows:

A mixture of (3-cyanopropyl)triphenylphosphonium bromide (41.0 g), ammonium chloride (6.69 g), lithium chloride (0.1 g) and sodium azide (8.13 g) in dry N,N-dimethylformamide (150 ml) was heated with stirring at 125° C. under argon for 18 hours. The mixture was cooled to ambient temperature, solid removed by filtration and the residue washed with N,N-dimethylformamide (50 ml). The combined filtrate and washings were evaporated. The yellow oil obtained was dissolved in water (100 ml) and kept for 16 hours at 4° C. The crystalline solid which had formed was collected and recrystallised from 50% v/v methanol/ether (200 ml) to give (3-[1(H)-tetrazol-5-yl]propyl)triphenylphosphonium bromide (26.15 g), m.p. 200°-202.5° C., NMR (90 MHz, d$_6$-DMSO): 2.07 (2H, m), 3.14 (2H, t J=8 Hz) 3.72 (2H, m), 7.86 (15 H, m).

EXAMPLE 5

A solution of 5-[3(Z)-5-(4-o-hydroxyphenyl-2,2-dimethyl-1,3-dioxan-cis-5-yl)pentenyl]-1(H)-tetrazole (666 mg) in isobutyraldehyde (1.76 ml) was treated with p-toluenesulphonic acid (5 mg) and stirred for 2 hours. Ether (50 ml) was then added and the mixture was extracted with 0.2M potassium hydroxide (3×15 ml). The combined aqueous extracts were acidified with acetic acid and then extracted with ether (3×30 ml). These combined extracts were washed with water (3×15 ml), then with saturated brine (2×15 ml), then dried (MgSO$_4$) and evaporated. The residue was purified by medium pressure liquid chromatography, eluting with hexane/ethyl acetate/acetic acid (50:50:1 v/v) to give 5-[3(Z)-5-([2,4,5-cis]-4-o-hydroxyphenyl-2-isopropyl-1,3-dioxan-5-yl)pentenyl]-1(H)-tetrazole, as a white, solid foam (458 mg); NMR: 1.04 (6H, d J=7 Hz), 1.82 (2H, m), 2.02 (2H, m), 2.58 (3H, m), 3.11 (2H, m), 3.96 (1H, dm J=11 Hz), 4.07 (1H, dd J=11, 1 Hz), 4.64 (1H, d J=4 Hz), 5.28 (1H, d J=2 Hz), 5.34 (2H, m), 6.87 (2H, m), 7.02 (1H, dd J=7, 1.5 Hz), 7.16 (1H, td J=7, 1.5 Hz); m/e 359 (M+H)$^+$, 358 (M$^+$).

EXAMPLES 6-8

A solution of 5-[3(Z)-5-(4-o-hydroxyphenyl-2,2-dimethyl-1,3-dioxan-cis-(5-yl)pentenyl]-1(H)-tetrazole (344 mg), o-chlorobenzaldehyde (169 mg) and p-toluenesulphonic acid (2 mg) in a mixture of dry toluene (2 ml) and THF (1 ml) was stirred for 24 hours. Ether (40 ml) was then added and the mixture was extracted with 0.1M potassium hydroxide (40 ml). The aqueous extract was acidified with acetic acid and then extracted with ether (3×20 ml). The combined extracts were washed with water (3×10 ml), then with saturated brine (2×10 ml), then dried (MgSO4) and evaporated. The residue was purified by medium pressure liquid chromatography, eluting with hexane/ethyl acetate/acetic acid (45:55:1 v/v) to give 5-[3(Z)-5-([2,4,5]-cis-2-o-chlorophenyl-4-o-hydroxyphenyl-1,3-dioxan-5-yl)pentenyl]-1(H)-tetrazole (Example 6), as a white, solid foam (211 mg); NMR: 1.95 (2H, m), 2.51 (2H, m), 2.77 (1H, m), 3.00 (2H, t J=8 Hz), 4.22 (2H, m), 5.42 (2H, m), 5.53 (1H, d J=2 Hz), 6.11 (1H, s), 6.82 (1H, bd J=8 Hz), 6.90 (1H, m), 7.15 (2H, m), 7.36 (3H, m), 7.72 (1H, m); m/e 426 (M+).

In a similar manner, but starting with o-cyanobenzaldehyde (157 mg) instead of o-chlorobenzaldehyde and carrying out the reaction for 3 days, there was obtained, after medium pressure liquid chromatography eluting with hexane/ethyl acetate/acetic acid (40:60:1 v/v), 5-[3(Z)-5-([2,4,5-cis]-2-o-cyanophenyl-4-o-hydroxyphenyl-1,3-dioxan-5-yl)pentenyl]-1(1H)-tetrazole (Example 7), as a white, solid foam (108 mg); NMR: 1.90 (2H, m), 2.35 (2H, m), 2.70 (1H, m), 3.03 (2H, m), 4.18 (2H, m), 5.26 (1H, m), 5.48 (1H, m), 5.49 (1H, d J=2 Hz), 5.83 (1H, s), 6.82 (1H, bd J=8 Hz), 6.88 (1H, td J=7, 1 Hz), 7.15 (2H, m), 7.61 (3H, m), 7.84 (1H, m); m/e 417 (M+).

In a similar manner, but starting with p-cyanobenzaldehyde (157 mg) and carrying out the reaction for 2 days, there was obtained after medium pressure column chromatography, eluting with hexane/ethyl acetate/acetic acid (35:65:1 v/v), 5-[3(Z)-5-([2,4,5-cis]-2-p-cycanophenyl-4-o-hydroxyphenyl-1,3-dioxan-5-yl)pentenyl]-1(H)-tetrazole (Example 8), as white, solid foam (166 mg); NMR: 1.86 (1H, m), 2.01 (1H, m), 2.42 (2H, m), 2.56 (1H, m), 3.00 (2H, m), 4.20 (2H, br s), 5.41 (2H, m), 5.49 (1H, d J=2 Hz), 5.81 (1H, s), 6.83 (1H, dd J=8, 1 Hz), 6.91 (1H, td J=7, 1 Hz), 7.16 (2H, m), 7.69 (4H, s); m/e 417 (M+).

Example 9

Illustrative pharmaceutical dosage forms include the following tablet and capsule formulations, which may be obtained using standard procedures:

|  | mg/tablet |
| --- | --- |
| TABLET I | |
| Compound X* | 5.0 |
| Lactose Ph. Eur | 89.25 |
| Croscarmellose sodium | 4.0 |
| Maize starch paste (5% w/v paste) | 0.75 |
| Magnesium stearate | 1.0 |
| TABLET II | |
| Compound X* | 100 |
| Lactose Ph. Eur | 182.75 |
| Croscarmellose sodium | 12.0 |
| Maize starch paste (5% w/v aqueous paste) | 2.25 |
| Magnesium stearate | 3.0 |
| CAPSULE | |
| Compound X* | 10 |
| Lactose Ph. Eur. | 488.5 |
| Magnesium stearate | 1.5 |

Note: Compound X* stands for a tetrazole derivative formula I, or a salt thereof, for example a compound of formula I described in any of the previous Examples.

Formulae
(Description)

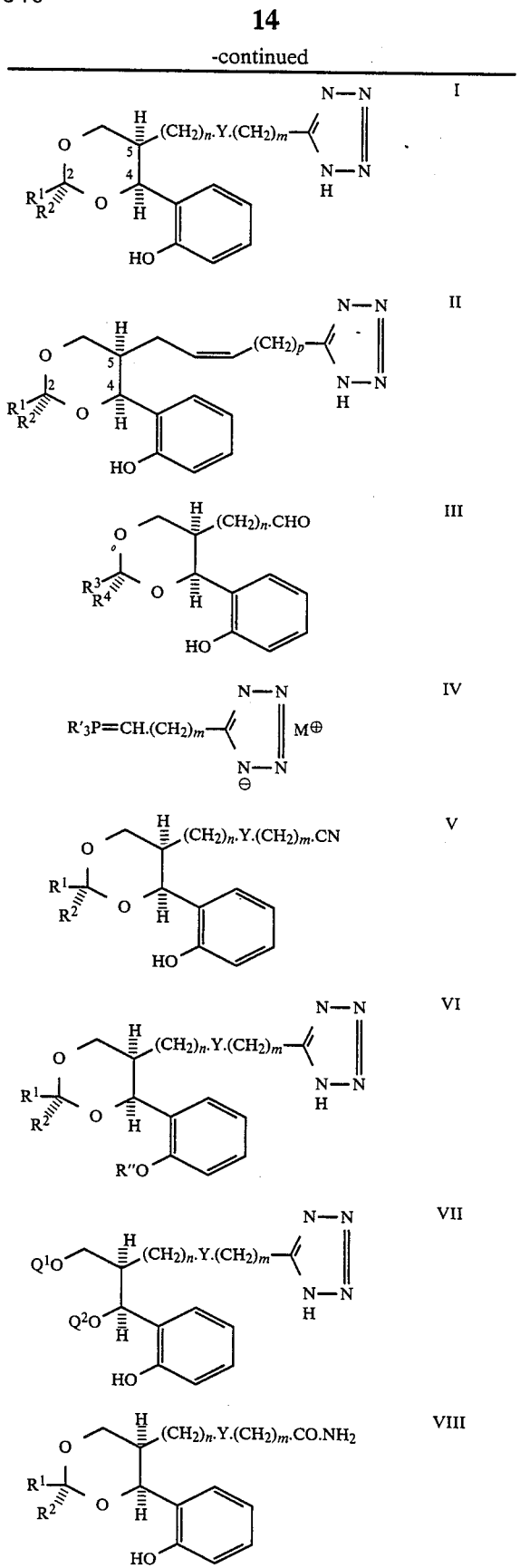

What is claimed is:

1. A 5-[(4-o-hydroxyphenyl-1,3-dioxan-5-yl)alkenyl]-1(H)-tetrazole of the formula I

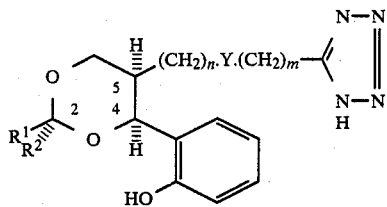

wherein $R^1$ and $R^2$ are independently selected from hydrogen, (1–6C)alkyl and trifluoromethyl, provided that $R^1$ and $R^2$ taken together contain no more than 6 carbon atoms; or $R^1$ is phenyl optionally bearing one or two substituents independently selected from halogeno, trifluoromethyl, cyano, nitro and (1–4C)alkoxy, and $R^2$ is hydrogen; Y is vinylene; n is 1 or 2; and m is 1, 2 or 3; and the groups at positions 4 and 5 of the dioxane ring in formula I have cis-relative stereochemistry; or a pharmaceutically acceptable salt thereof.

2. A compound as claimed in claim 1 wherein $R^1$ and $R^2$ are independently selected from hydrogen, methyl, ethyl, propyl, isopropyl, butyl, t-butyl and trifluoromethyl, provided $R^1$ and $R^2$ together contain no more than 6 carbon atoms; or $R^1$ is phenyl optionally bearing one or two substituents independently selected from fluoro, chloro, bromo, trifluoromethyl, cyano, nitro, methoxy and ethoxy, and $R^2$ is hydrogen.

3. A compound as claimed in claim 1 wherein $R^1$ is hydrogen, methyl, ethyl, isopropyl, t-butyl or trifluoromethyl and $R^2$ is hydrogen, methyl or trifluoromethyl; or $R^1$ is phenyl optionally bearing one or two substituents independently selected from halogeno, trifluoromethyl, cyano, nitro and (1–4C) alkoxy, and $R^2$ is hydrogen.

4. A compound as claimed in claim 1, wherein Y is cis-vinylene, n is 1 and m is 2 or 3.

5. A compound of the formula II

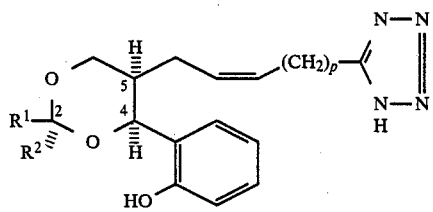

wherein $R^3$ and $R^4$ are both methyl; or $R^3$ is isopropyl, t-butyl, trifluoromethyl or phenyl bearing a chloro or cyano substituent, and $R^4$ is hydrogen; p is 2 to 3; and the groups at positions 4 and 5 of the dioxane ring in formula II have cis-relative stereochemistry; or a pharmaceutically acceptable salt thereof.

6. A compound selected from 5-[3(Z)-5-([2,4,5-cis]-4-o-hydroxyphenyl-2-isopropyl-1,3-dioxan-5-yl(pentenyl]-1(H)-tetrazole, 5-[3(Z)-5-([2,4,5-cis]-2-p-cyanophenyl-4-o-hydroxyphenyl-1,3-dioxan-5-yl)pententyl]-1(H)-tetrazole, and the pharmaceutically acceptable salts thereof.

7. A salt as claimed in claim 1 or 5 which is selected from sodium, potassium, magnesium, calcium, aluminium and ammonium salts, and from salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethyl ammonium hydroxide.

8. A method of antagonising one or more of the actions of thromboxane $A_2$ in a warm-blooded animal requiring such treatment, which comprises administering to the said animal an effective amount of a compound of the formula I or II, or a pharmaceutically acceptable salt thereof, as defined in claim 1 or 5.

9. A pharmaceutical composition which comprises a compound of formula I, or a pharmaceutically acceptable salt thereof, as claimed in claim 1 or 5, together with a pharmaceutically acceptable salt thereof.

10. A compound of the formula II

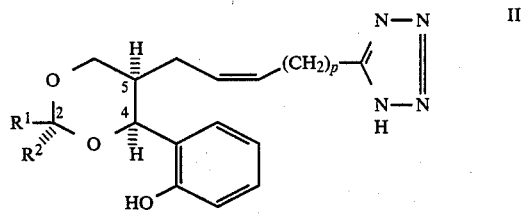

wherein $R^3$ and $R^4$ are both methyl; or $R^3$ is isopropyl, t-butyl, trifluoromethyl or phenyl bearing a chloro or cyano substituent, and $R^4$ is hydrogen; p is 2; and the groups at positions 4 and 5 of the dioxane ring in formula II have cis-relative stereochemistry; or a pharmaceutically acceptable salt thereof.

11. A compound as claimed in claim 1 wherein $R^1$ is hydrogen, methyl, ethyl, isopropyl, t-butyl or trifluoromethyl and $R^2$ is hydrogen, methyl or trifluoromethyl; or $R^1$ is phenyl optionally bearing one or two substituents independently selected fron fluoro, chloro, bromo, trifluoromethyl, cyano, nitro, methoxy and ethoxy, and $R^2$ is hydrogen.

* * * * *